(12) United States Patent  
Ripanti

(10) Patent No.: US 11,117,171 B2  
(45) Date of Patent: Sep. 14, 2021

(54) ACCESSORY STRUCTURE FOR A TATTOO MACHINE

(71) Applicant: Tiziano Ripanti, Ancona (IT)

(72) Inventor: Tiziano Ripanti, Ancona (IT)

( * ) Notice: Subject to any disclaimer, the term of this patent is extended or adjusted under 35 U.S.C. 154(b) by 146 days.

(21) Appl. No.: 16/258,212

(22) Filed: Jan. 25, 2019

(65) Prior Publication Data

US 2019/0232340 A1 Aug. 1, 2019

(30) Foreign Application Priority Data

Jan. 26, 2018 (IT) .......................... 102018000001927

(51) Int. Cl.
*B08B 3/04* (2006.01)
*A61M 37/00* (2006.01)
*A61M 35/00* (2006.01)

(52) U.S. Cl.
CPC ............. *B08B 3/04* (2013.01); *A61M 35/003* (2013.01); *A61M 37/0076* (2013.01); *A61M 2209/10* (2013.01)

(58) Field of Classification Search
CPC combination set(s) only.
See application file for complete search history.

(56) References Cited

U.S. PATENT DOCUMENTS

| 5,054,339 A * | 10/1991 | Yacowitz .......... A61M 37/0076 604/47 |
| 2003/0212415 A1 | 11/2003 | Karasiuk |
| 2007/0156095 A1 | 7/2007 | Hazut et al. |
| 2013/0072867 A1* | 3/2013 | Dakin ..................... A01N 59/08 604/78 |
| 2013/0123746 A1* | 5/2013 | Bunting ................ A61M 5/142 604/506 |
| 2016/0287813 A1* | 10/2016 | Leibovici ................ A61M 5/42 5/422 |

FOREIGN PATENT DOCUMENTS

| AT | 14 817 | 6/2016 |
| WO | WO 2017/094005 | 6/2017 |

* cited by examiner

*Primary Examiner* — Cristi J Tate-Sims
(74) *Attorney, Agent, or Firm* — Leason Ellis LLP

(57) ABSTRACT

Accessory structure for a tattoo machine, comprising supplier means (10) and/or means (8) for supplying and/or ejecting a detergent liquid (11) with a nozzle (9) applied using holding means (6) near the colouring needles (4) with reciprocating motion or provided terminating therein, said supplier means (10) and/or ejector means (8) being supplied by a detergent liquid reservoir (13) and pumping means (16, 17, 18) actuated by the operator.

4 Claims, 1 Drawing Sheet

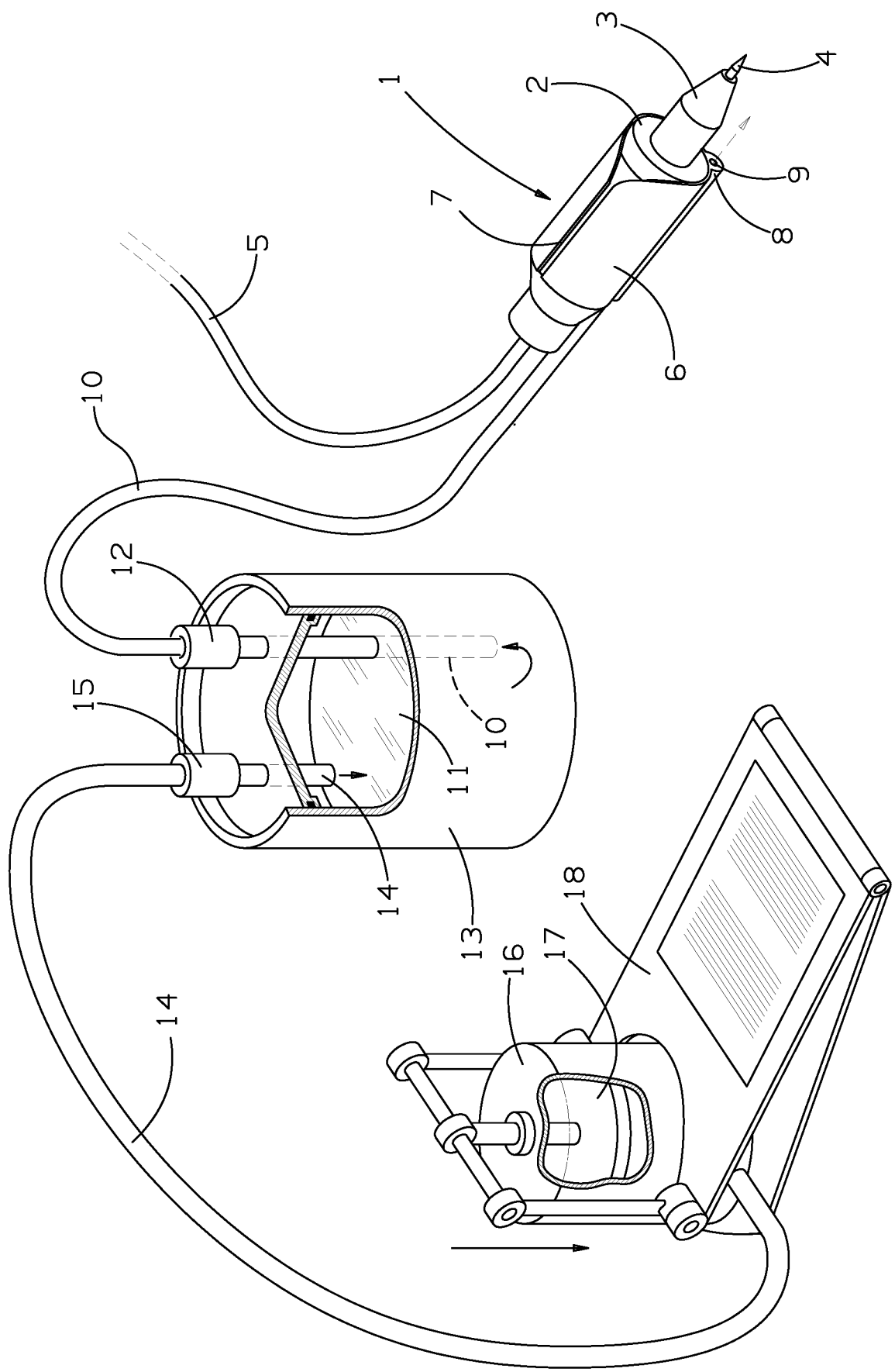

ACCESSORY STRUCTURE FOR A TATTOO MACHINE

CROSS-REFERENCE TO RELATED APPLICATIONS

This application claims priority from Italian Patent Application No. 102018000001927 filed on Jan. 26, 2018, the disclosure of which is expressly incorporated by reference.

DETAILED DESCRIPTION

Field of the Art

The tattoo machine is an electrical device handled by the tattoo artist for tendentially permanent decoration of the human body by introducing pigments under the epidermis into the dermis.

The prior art substantially reveals two types of functionally different tattoo machines and various aesthetically different machines:

a classic type using a system of cores electromagnetic with the aim of determining a reciprocating linear motion with respect to a metal bar, at whose top part there is fixed one or more needles;

a relatively innovative type with a reciprocating electric motor, even with variable power by means of a potentiometer, defined "rotary", which imparts a reciprocating motion to a fitting to which there can be interchangeably coupled heads or so-called needle-holder cartridges; the interchangeability allowing to change the setting and use for different functions, for example both for outlining and colouring the conceived drawing, without necessarily requiring two machines.

In any case, in their alternating motion the needles fixed to the machine, irrespective of the type, penetrate into the skin leaving the pigments in the dermis in the layer beneath the epidermis and not subject to continuous tissue replacement, which could cause the deterioration of the tattoo within a short period of time.

Irrespective of the mechanical instrument used, the tattoo artist constantly needs to clean the surface of the skin on which he/she is drawing of residual pigments and leaking blood, which form continuously and quickly thus preventing him/her from clearly seeing and distinguishing the work area whereas this would instead obviously be indispensable for the quality of the work.

As concerns this, tattoo artists use a very empiric technique. They place the machine on a surface, usually a translatable and orientable machine within the reach of the arm, from which they take a container containing the detergent liquid, normally a common spray bottle with an actuation trigger, they spray the part in question, they dry it and clean using a swab which they always hold with the other hand, and then they pick up the machine once again and continue working and so on and so forth.

Requiring the operator to continuously change the tool, unless being helped by an assistant, this technique is intuitively uncomfortable and dispersive; especially when the operator has to work on parts of the body that do not allow him/her to stay at a comfortable position, for example as concerns tattoos to be drawn on the back of persons laying down.

Objects of the Invention

Thus, in this context an object of the present invention is to provide an innovative and functional device suitable to allow tattoo artists to carry out the work without having to interrupt constantly to spray the work area, or at least eliminate the need of placing the machine down to pick the container of the detergent liquid.

Another object of the present invention is to achieve the aforementioned objective through a solution suitable to adapt to existing tattoo machines, irrespective of the type, as well as suitable to be incorporated in machines contingently designed to use it.

Still a further object of the present invention is to attain any one of the aforementioned objects through a device that is simple and efficient, safe to use and relatively inexpensive considering the actual results attained therewith.

Summary of the Solution Concept

These and other objects are all attained by means of the accessory structure for a tattoo machine according to the present invention as defined by the claims outlined at the bottom of the present description text, comprising supplier means (10) and/or means (8) for supplying and/or ejecting a detergent liquid (11) with a nozzle (9) applied using holding means (6) near the colouring needles (4) with reciprocating motion or provided terminating therein, said supplier means (10) and/or ejector means (8) being supplied by a detergent liquid reservoir (13) and manual or automatic pumping means (16, 17, 18) actuated by the operator.

Description of the Attached Drawings

Further characteristics and advantages of the accessory structure for a tattoo machine according to the present invention, will be more apparent from the following detailed description of a relative preferred but non-exclusive embodiment, represented solely by way of non-limiting example in the only attached drawing, schematically illustrated in which is a tattoo machine of the rotary type with the device according to the present invention associated thereto, also schematised.

Static Description of the Embodiment

With reference to such figure, a tattoo machine of the s-called rotary type, of any known type, for example pen-shaped with a cylindrical holding body 2, apically fitted on which is an interchangeable head or cartridge 3, carrying one or more needles 4, reciprocatingly moved in the axial direction by electric drive means—not illustrated—inside the body 2, of the known type and in the known manner, power-supplied by means of proximal wiring 5 to a transformer and thus the power supply mains, is indicated in its entirety with 1.

In the embodiment of the present invention described and illustrated by way of example, the pen 2 is elastically wrapped by a flexible casing 6, that can also be defined as a coating jacket 6, or a shell 6, substantially cylindrical, preferably made of plastic material, of the type appropriate/approved for health/medical use.

The elastic casing 6 has a longitudinal through cut 7, or gap portion 7, to confer it ease of application dilation against the elastic deformation thereof and, in a diametrically opposite arrangement, a thickening portion 8, in which there is obtained a longitudinally through duct indicated using the same reference number 8, apically terminating in a dispenser nozzle 9 near the needle 4 and proximally connected to a pipe 10 for delivering a liquid 11.

The pipe 10, after the possible interposition of a one-way valve or check valve 12, draws from a bellow-like reservoir 13, that can be sealingly closed, containing water or detergent liquid 11 suitable for the purpose.

Supplying into the tank 13, after interposing a relative one-way valve or check valve 15, is another air supply pipe 14, connected to a displacement pump 16 with plunger 17 actuated by a pedal 18, for the purposes outlined below.

Dynamic Description of the Embodiment

Thus, having completed the static description of a preferred embodiment of the accessory structure for a tattoo machine according to the present invention, following is the dynamic description of the same, i.e. the relative operation.

The elastic shell 6, which can be provided with a roughened anti-slip surface both inside and outside, can be easily dilated against the elasticity thereof and released to wrap the body of the machine 1, thus intertwining stably therewith; obviously, such configuration allows to wrap cylindrical structures of different dimensions from among the various pen-equipped tattoo machine models available in the market, even considering that the relative diameters vary limitedly in the market, considering the common purpose of gripping and holding by a human hand.

The increase of the diameter that the shell confers to the holding and gripping of the tool is rather insignificant; in addition, this does not add any principle or factual-based limitation, solely considering that, empirically, many tattoo artists thicken the gripping element of the machines available in the market using tapes or the like, so as to increase the gripping and holding diameter, so that the handling of the tool can be less tiring during the long work sessions.

In the other type of tattoo machines, those not having an exclusively cylindrical pen-like shape, irrespective of how they are shaped and driven, there is, and obviously just like there could be not, a portion to be gripped by the operator near the operating apex and penetration needles, at times interchangeable and of the disposable type, specifically described hereinafter in the alternative embodiments;

in any alternative embodiment of the tattoo machines, it is thus possible to provide for an elastic shell of the self-wrapping type around the gripping element, with length and diameter appropriate to cover the gripping element or portion thereof and move and keep the sprayer nozzle near the penetration needles.

Thus, any type of tattoo machine used, the user stations near the needles 4 of a sprayer nozzle 9, to which he/she can supply a detergent liquid 11 by means of the pump 16 actuated by a pedal 18, which places in overpressure the air in the pneumatically sealed bellow-like reservoir 13 of the detergent liquid 11, thus pushed to flow into the pipes 10 and 8 and reach the nozzle 9, from which it can be sprayed when needed on the portion of the epidermis being decorated, without having to place the machine down and grip a special spray container, thus reducing the need for relative interruptions relative and thus the ensuing waste of time and concentration; while with the other hand, which remains unoccupied like in the prior art, the operator can clean using the swab, like it already usually occurs.

Alternative Embodiments

It is obvious that in further alternative embodiments still falling within the innovation concept subject of the embodiment illustrated above and claimed below, the accessory structure for a tattoo machine according to the present invention, may be implemented through equivalent technical and mechanical means, i.e. with further supplementary solutions, same case applying to application parameters that can be varied to suit the purpose;

in particular:

the illustrated embodiment or the further mentioned embodiments are conceived for the application of the accessory according to the present invention to pre-existing tattoo machines not explicitly designed to receive it;

obviously, in tattoo machines specifically designed for applying this solution, the supply pipe and sprayer nozzle near the needles can be incorporated from the origin in the elements forming the machine, of any kind, type and shape, thus tendentially slimmer, easier to handle and comfortable to use.

Same case applies, mutatis mutandis, to tattoo machines of the core type which provide for an interchangeable grip of the disposable type for hygiene purposes; in such distinctive technological actuations, though the alternative embodiment of the present invention being applicable, of polyvalent applications of a cannula retention shell around the gripping element, may actually and simply—in an alternative embodiment—provide for a longitudinal hole in the disposable gripping element for the through-passing of the cannula and supply of the nozzle near the needles, or provide for a disposable gripping element already provided with accessories for the implementation of the present invention.

On the other hand, the detergent liquid storage, reservoir and supply means may be of any kind and type suitable for the purpose, different from the manual one described by way of example described in the design context of an extremely simple and inexpensive tool:

as a matter of fact, there can be designed and applied manual or automatic pumps of any kind and type suitable for the purpose acting indirectly on the air or directly on the detergent fluid to be conveyed.

In the embodiment dedicated to pre-existing tattoo machines, the retention system in the position of the sprayer nozzle can alternatively be conceived in any manner suitable for the purpose.

Advantages of the Invention

As observable from the preceding detailed description of a preferred embodiment, the accessory structure for a tattoo machine according to the present invention offers advantages corresponding to the attainment of these and other pre-set objects:

as a matter of fact, there is integrated a functional, modular, polyvalent and inexpensive solution suitable to facilitate the art of tattoo from an operating and hygienic point of view.

KEY TO REFERENCE NUMBERS 1) tattoo machine in its entirety
2) cylindrical body of the tattoo machine
3) interchangeable head of cartridge of the tattoo machine
4) apical needle
5) network power supply wiring of the electric motor of the tattoo machine
6) flexible casing or coating jacket of the cylindrical body of the tattoo machine
7) longitudinal through cut or gap portion of the flexible casing or coating jacket of the cylindrical body of the tattoo machine 8) duct obtained in the thickness of the flexible casing or coating jacket of the cylindrical body of the tattoo machine
9) nozzle of the duct obtained in the thickness of the flexible casing or coating jacket of the cylindrical body of the tattoo machine
10) detergent liquid delivery pipe
11) detergent liquid
12) check valve of the detergent liquid delivery pipe
13) pneumatically sealed bellow-like reservoir for the detergent liquid
14) pipe for supplying air to the bellow-like reservoir
15) check valve of the pipe for supplying air to the bellow-like reservoir
16) displacement plunger pump
17) plunger of the displacement plunger pump
18) actuation pedal of the displacement plunger pump

The invention claimed is:

1. Accessory structure for a tattoo machine with an electromagnetic or electric actuator suitable to directly or indirectly determine a reciprocating linear motion in at least one needle carried apically on the machine in a gripping element (2), characterised in that the accessory structure comprises removable holding means (6) suitable to detachably enclose the gripping element (2) or a portion thereof, said holding means (6) being provided with a longitudinal through duct (8) which is apically terminating in a dispenser nozzle (9) near the needle (4) and proximally connected to a piping (10) for supplying a detergent liquid (11) to the dispenser nozzle (9).

2. Accessory structure according to claim 1, wherein said holding means (6) consists of elastic means suitable to stably wrap around the gripping element (2) of the machine or a portion thereof.

3. Accessory structure according to claim 2, wherein said holding means (6) suitable to enclose the gripping element (2) is made up of a flexible casing or coating jacket or shell with longitudinal through cut (7) or longitudinal gap portion.

4. Accessory structure according to claim 3, wherein said through duct (8) is provided on a thickness of said holding means (6) apically terminating in the dispenser nozzle (9) near the needle (4).

* * * * *